US008129676B2

(12) United States Patent
Vestel et al.

(10) Patent No.: US 8,129,676 B2
(45) Date of Patent: Mar. 6, 2012

(54) SURFACE ENHANCED RAMAN SPECTROSCOPY DETECTION WITH ION SEPARATION PRE-FILTER

(75) Inventors: Michael Vestel, San Francisco, CA (US); Caterina Netti, Glasgow (GB); Erkinjon Nazarov, Lexington, MA (US); Gareth S. Dobson, Burlingame, CA (US); Stephen L. Coy, Wayland, MA (US); Richard Copeland, Palo Alto, CA (US); Michael Coggiola, Sunnyvale, CA (US); Lawrence Dubois, Danbury, CT (US); Alexander Hallock, Redwood City, CA (US); Joseph R. Stetter, Hayward, CA (US)

(73) Assignees: SRI International, Menlo Park, CA (US); DH Technologies Development Pte. Ltd., Singapore (SG); Renishaw Diagnostics Limited, Glasgow (GB)

( * ) Notice: Subject to any disclaimer, the term of this patent is extended or adjusted under 35 U.S.C. 154(b) by 169 days.

(21) Appl. No.: 12/448,795

(22) PCT Filed: Dec. 17, 2007

(86) PCT No.: PCT/US2007/025929
§ 371 (c)(1),
(2), (4) Date: Mar. 19, 2010

(87) PCT Pub. No.: WO2008/085357
PCT Pub. Date: Jul. 17, 2008

(65) Prior Publication Data
US 2011/0266429 A1    Nov. 3, 2011

Related U.S. Application Data

(60) Provisional application No. 60/878,902, filed on Jan. 5, 2007.

(51) Int. Cl.
*B01D 59/44* (2006.01)
*H01J 49/40* (2006.01)
*H01J 49/16* (2006.01)

(52) U.S. Cl. ........ 250/288; 250/281; 250/282; 250/286; 250/287; 250/423 R; 250/424

(58) Field of Classification Search ............... 250/288, 250/281, 282, 286, 287, 423 R, 424
See application file for complete search history.

(56) References Cited

U.S. PATENT DOCUMENTS

| | | | | |
|---|---|---|---|---|
| 6,815,668 | B2 * | 11/2004 | Miller et al. | 250/286 |
| 7,005,632 | B2 * | 2/2006 | Miller et al. | 250/287 |
| 7,361,890 | B2 * | 4/2008 | Patterson | 250/288 |
| 7,608,818 | B2 * | 10/2009 | Miller et al. | 250/288 |
| 2004/0094704 | A1 | 5/2004 | Miller et al. | |
| 2006/0071665 | A1 | 4/2006 | Blake et al. | |

OTHER PUBLICATIONS

Sylvia, et al. Surface-Enhanced Raman Detection of 2,4-Dinitrotoluene Impurity Vapor as a Marker to Locate Landmines, Anal. Chem. 2000, 72, 5834-5840. Baker et al. Progress in plasmonic engineering of surface-enhanced Raman-scattering substrates toward ultra-trace analysis, Anal Bioanal Chem (2005) 382: 1751-1770.
Clarkson et al. A theoretical study of the structure and vibrations of 2,4,6-trinitrotoluene, Journal of Molecular Structure 648 (2003) 203-214.
Kneipp et al. Near-infrared surface-enhanced Raman scattering of trinitrotoluene on colloidal gold and silver, SpectrochimicaActa Part A 51 (1995)2171-2175.

* cited by examiner

*Primary Examiner* — Nikita Wells
(74) *Attorney, Agent, or Firm* — Lumen Patent Firm

(57) ABSTRACT

Detecting and identifying ions using surface enhanced Raman spectroscopy (SERS) and an ion separation pre-filter, such as an ion spectrometer, are provided. The combination of an ion separator as a pre-filter for SERS provides a highly sensitive detector with very low false alarm rates. Target ions from an ionized sample are identified and separated by the ion separator. The target ions are steered and deposited onto a SERS substrate for Raman spectroscopic analysis with an optical probe. The Raman spectrum is compared with reference spectra and the composition of the sample is identified. The ion current from the target ions can also be measured, preferably concurrently with the Raman spectrum measurement. Types of ion separators include a differential ion mobility spectrometer, an ion mobility spectrometer, or a mass spectrometer.

20 Claims, 4 Drawing Sheets

SURFACE ENHANCED RAMAN SPECTROSCOPY DETECTION WITH ION SEPARATION PRE-FILTER

CROSS-REFERENCE TO RELATED APPLICATIONS

This application is a 371 of PCT Patent Application PCT/US2007/025929 filed Dec. 17, 2007, which claims the benefit of U.S. Provisional Application 60/878,902 filed Jan. 5, 2007.

FIELD OF THE INVENTION

The invention relates generally to chemical detection. More particularly, the present invention relates to the identification of ions using surface enhanced Raman spectroscopy (SERS) combined with an ion separation pre-filter.

BACKGROUND

Industries, including security and defense, require instruments to detect and identify a variety of compounds, including toxic industrial chemicals and materials, explosives, chemical warfare agents (CWA), biological agents and other potentially dangerous agents. Due to the current heightened fears of terrorist activity, highly sensitive, selective, and accurate detecting instruments are particularly desired for security screening purposes, such as in airports.

The instruments currently employed for detection of explosives and CWAs include ion mobility spectrometers, mass spectrometers, liquid chromatographs, and gas chromatographs. These instruments, however, have low sensitivity and low selectivity; consequently, they suffer from high false alarm rates. A measure of the sensitivity of a detector is its limit of detection. In the case of the currently employed technologies, the limit of detection can be significant, thereby allowing trace chemicals to go undetected.

In addition to having low sensitivity, the current instruments also suffer from high false alarm rates. False positive alarms can be time-consuming and cause delays in the screening process. More importantly, high false alarm rates reduce the confidence of the user in the instrument producing the false alarms, which discourages the user from using the instrument. Obviously, security suffers when the detecting instrument is not utilized.

Recently, Surface Enhanced Raman Spectroscopy (SERS) has been developed for the detection of molecules with extreme sensitivity. In principle, the limit of detection for SERS is as low as a single molecule, though this is not realized in field conditions. SERS also has a very high molecular discrimination capability due to the intrinsic nature of the Raman scattering. SERS requires the deposition of particles to be identified onto a textured metal surface or substrate. The presence of a large variety of compounds can create problems from high field contamination because the Raman spectroscopic signatures become unclear or unidentifiable.

The present invention addresses the problem of detecting and identifying compounds. The present invention advances the art with a SERS ion detector with an ion separation pre-filter.

SUMMARY OF THE INVENTION

The present invention is directed to detection and identification of ions formed in the ionization of an analyte sample with a SERS system and an ion separation pre-filter. An ion separator is used to separate target ions to be identified from different ion species. The target ions are steered and deposited onto a SERS substrate. An optical probe measures a spectroscopic signal of the substrate with the deposited ions. In particular, the spectroscopic signal is a molecular vibrational spectrum, i.e. a Raman spectrum. A computer compares the measured signal with a library of stored signals to identify the analyte.

The ion separator can be a differential ion mobility spectrometer, an ion mobility spectrometer, or a mass spectrometer. Additional ion identification instruments, such as gas chromatographs and liquid chromatographs, can be used in combination with the ion separator to more effectively distinguish and separate the ions. The present invention can also have a detector electrode for measuring the ion current from the target ions. The detector electrode can include an electron multiplier, a photomultiplier, or an amplification circuit to improve the ion current measurement. The total ion current can be used to detect ions without the operation of the SERS system. Preferably, the SERS substrate can be used as the detector electrode and both the ion current measurement and the spectroscopic signal measurement can occur essentially simultaneously.

Additional components to improve the performance of the present invention include a flow-producing means, a cooling means, and a focusing means. A fan can produce gas flow away from the SERS substrate to reduce the contamination of the SERS substrate by neutral particles. By cooling the substrate, the ions are efficiently deposited onto the substrate and the Raman detection sensitivity is increased. Focusing the target ions onto a deposition area of the substrate can further improve the detector by increasing the density of target ions to be identified.

Multiple component analysis can be accomplished by dividing the SERS substrate into multiple segments separated by an insulator. With target ions deposited on each segment, the optical probe can measure the spectroscopic signal of each segment separately. The different segments can also have different substrate properties and/or probe settings. The multiple segments and optical probe can also allow imaging and detection of the whole segment area.

With an ion spectrometer as a pre-filter to select target ions, a highly sensitive SERS system can be used to verify the identity of the target ions with a high degree of confidence and a very low false alarm rate. In other words, the ion spectrometer solves contamination problems of SERS, whereas SERS alleviates the high false alarm rate of ion spectrometer detectors.

BRIEF DESCRIPTION OF THE FIGURES

The present invention together with its objectives and advantages will be understood by reading the following description in conjunction with the drawings, in which.

DETAILED DESCRIPTION OF THE INVENTION

Detection of trace agents is required for a great deal of security and industrial purposes. The success of detectors is measured by their sensitivity and false alarm rates with the ideal detector having a very low limit of detection and giving no false alarms. Below is a detailed description of a surface enhanced Raman spectroscopy (SERS) detector with an ion separation pre-filter for sensitive detection and identification of ions with low false alarm rates.

Figure 1:
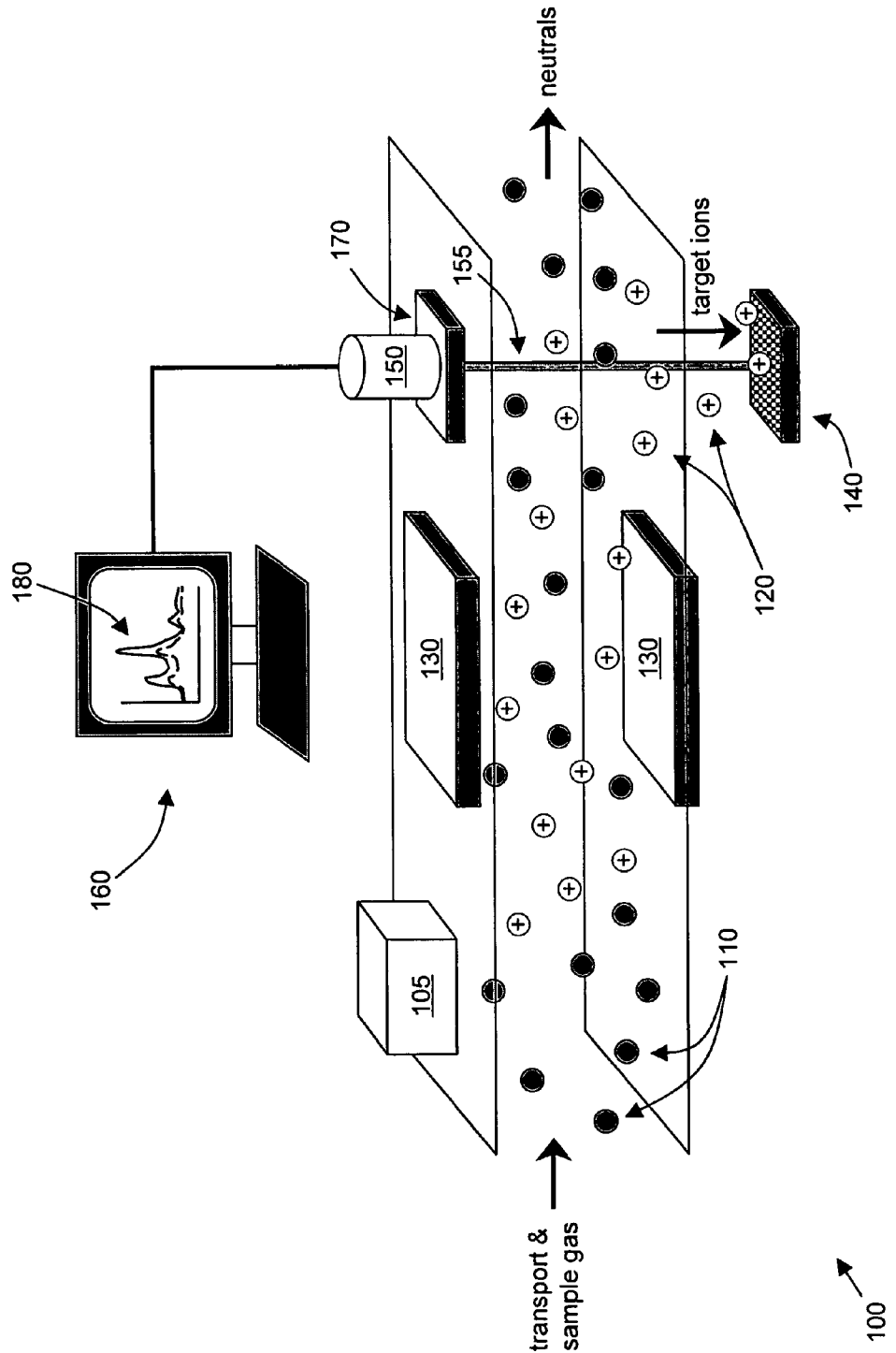
FIG. 1 shows an example of a surface enhanced Raman spectroscopy (SERS) device with an ion separation pre-filter for detecting and identifying ions according to the present invention.

FIG. 1 shows an example of a device 100 with high selectivity for ion detection and identification using a SERS system and an ion spectrometer pre-filter. In FIG. 1, a gas of transport particles and sample particles are introduced into the device from the left and the sample particles are ionized by an ionization source 105. The gas flow delivers the charged 120 and neutral 110 particles to an ion separator. The ion separator identifies and separates target ions from multiple ion species for delivery of the target ions to the SERS system. The selection of target ions by the ion separator depends on physical parameters of the ions, such as the ion mobility. The ion separator can operate essentially continuously. The target ions are steered into the SERS system.

The SERS system provides identity verification for the target ions to reduce or eliminate false alarms that may plague an ion separator by itself. In other words, the ion separator and the SERS system act as orthogonal detection means with the ion separator as a pre-filter for SERS. The SERS system includes a SERS substrate 140, an optical probe 150, and a computing means 160. The target ions are steered and deposited onto the SERS substrate 140. The optical probe 150 measures a spectroscopic signal 180 by exciting the SERS substrate 140 and measuring the molecular signal, such as the Raman scattering signal. This signal is unique for each molecule and provides an unambiguous identification of the molecular or ion species. The optical probe 150 generally employs a laser 155. The spectroscopic signal 180 is transmitted to the computing means 160, such as a computer, for identification of the signal 180. A library of reference spectroscopic signals is stored on the computer 160 or is accessible by the computer 160. The measured spectroscopic signal 180 is compared with the reference signals to identify the measured signal 180.

Figure 2:
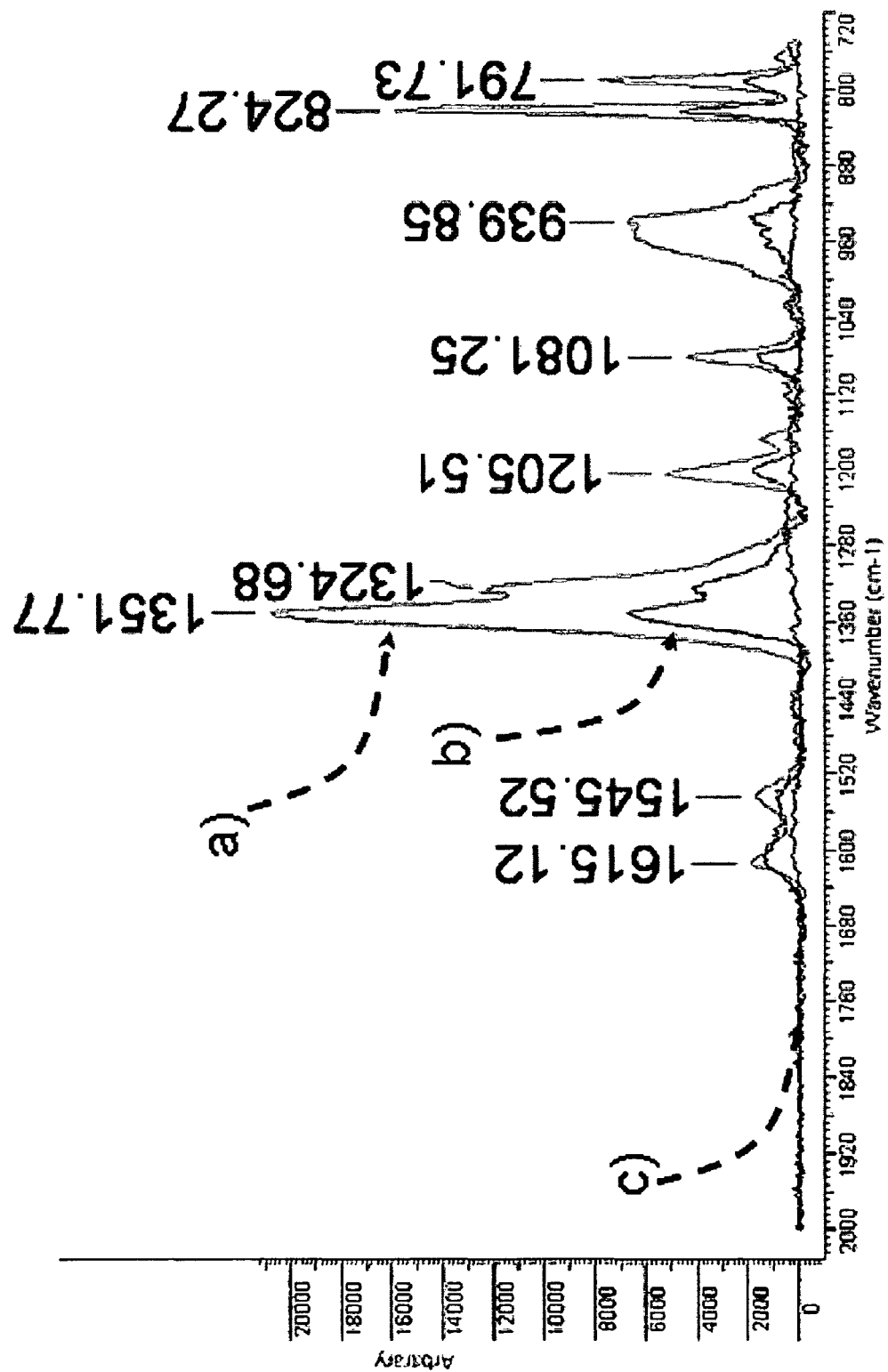
FIG. 2 shows an example of a measured Raman spectroscopic signal from a device of the present invention and a reference signal for identifying the measured Raman signal.

FIG. 2 shows plots for identifying a sample based on the spectroscopic measurements of the device of FIG. 1. The background spectrum, where no particles have been deposited onto the SERS substrate, is shown by FIG. 2(c). FIG. 2(a) shows a reference spectrum measured from a SERS substrate with dissolved TNT deposited directly onto the substrate. The spectrum of FIG. 2(b) was measured from a SERS substrate with deposited ions, where the deposited ions are from an ionized solid sample and selected as target ions by an ion spectrometer pre-filter. The peaks in the spectroscopic signal to be identified align with the peaks of the reference spectroscopic signal. In this example, the Raman "fingerprint" clearly identifies that the sample contains TNT.

In a preferred embodiment, the library of reference spectroscopic signals include spectra of an explosive, a homemade explosive, a flammable liquid, a chemical warfare agent, a chemical agent, a biological agent, a biochemical agent, a toxic industrial chemical, a toxic industrial material, an organic material, or any combination thereof. The device 100 is preferably for industrial, analytical, military, or security purposes. In particular, the device 100 can be used for airport screening.

The operation of the present invention is independent of the source of ionization. In a preferred embodiment, heating is used for controlled sublimation of a sample to be analyzed. The gaseous sample is then ionized by an ionization source 105. Ionization sources 105 include a corona source, a radioactive source, or an electrospray device. A preferred embodiment uses a film of $Ni^{63}$ as a radioactive ionization source.

Optionally, the device can be operated at elevated temperatures to help reduce precipitation. A neutral gas, which can be air, nitrogen, helium, argon, xenon or any combination thereof, flows through the device 100 and helps to direct the ions to the ion separator.

The ion separator can be a mass spectrometer, an ion mobility spectrometer, a differential ion mobility spectrometer (DMS), or any other device capable of separating target ions from multiple ion species. Optionally, the ion separator can include an additional ion filter. The ion filter can perform gas chromatography, liquid chromatography, or a combination thereof.

FIG. 1 shows a SERS ion detecting and identifying device 100 with a DMS pre-filter as the ion separator. Differential ion mobility spectroscopy requires the application of a radiofrequency (RF) voltage superimposed with a DC compensation voltage. In FIG. 1, electrodes 130 produce the RF voltage, thereby forming an asymmetric waveform RF electric field for inducing wave-like trajectories of the ions. The SERS substrate 140 can function as a detector electrode and, in combination with a deflector electrode 170, can produce the compensation voltage. The detector electrode and a deflector electrode 170 can also be used to establish a voltage gradient to steer and deposit the target ions onto the SERS substrate 140.

DMS spectrometers identify ions based on their trajectories from a particular combination of RF voltage and compensation voltage or ranges of RF and compensation voltages. The use of a specific combination of RF and compensation voltages can allow isolation of a single compound of the sample from a multi-component mixture due to the differences in the ion mobility of different compounds. The RF and compensation voltages can be any value and generally depend on the compounds to be identified and the geometry and dimensions of the device. In a preferred embodiment, the RF voltage produces a RF electric field ranging in strength from about 0 V/cm to about 25000 V/cm and the compensation voltage produces a DC electric field ranging in strength from about 20 V/cm to about 30 V/cm.

In addition to producing the compensation voltage and steering the target ions, the detector electrode can also be used to measure the current of the target ions. In FIG. 1 the SERS substrate 140 is a detector electrode, however another electrode can be used as a detector electrode for ion current measurement. By measuring the total ion current, the device is capable of detecting ions in a similar fashion as a conventional DMS device. The neutral particles and ions of species other than the target ion species will not be absorbed onto the detector electrode and will not contribute to the detected ion current. Even without the identity verification by the SERS system, the device is still capable of identifying and selectively detecting compounds based on an ion current analysis of the target ions. In other words, the SERS system can be operated continuously with the ion separator or only when verification or additional sensitivity is desired. The SERS system is especially necessary when detection is required in an environment with high levels of interferences.

It is important to note that the measurement of the target ion current by the detector electrode and the measurement of the spectroscopic signal by the SERS system can be accomplished approximately simultaneously. The approximate simultaneity of the measurements imply that the same batch of ions are used for the ion current measurement as the SERS spectroscopic measurement allowing for faster detection and consumption of lesser amounts of the sample compared with detectors with sequential measurements. The detector electrode can also include an electron multiplier, a photomultiplier, an amplification circuit, or any combination thereof for improving the ion current analysis.

Figure 3:
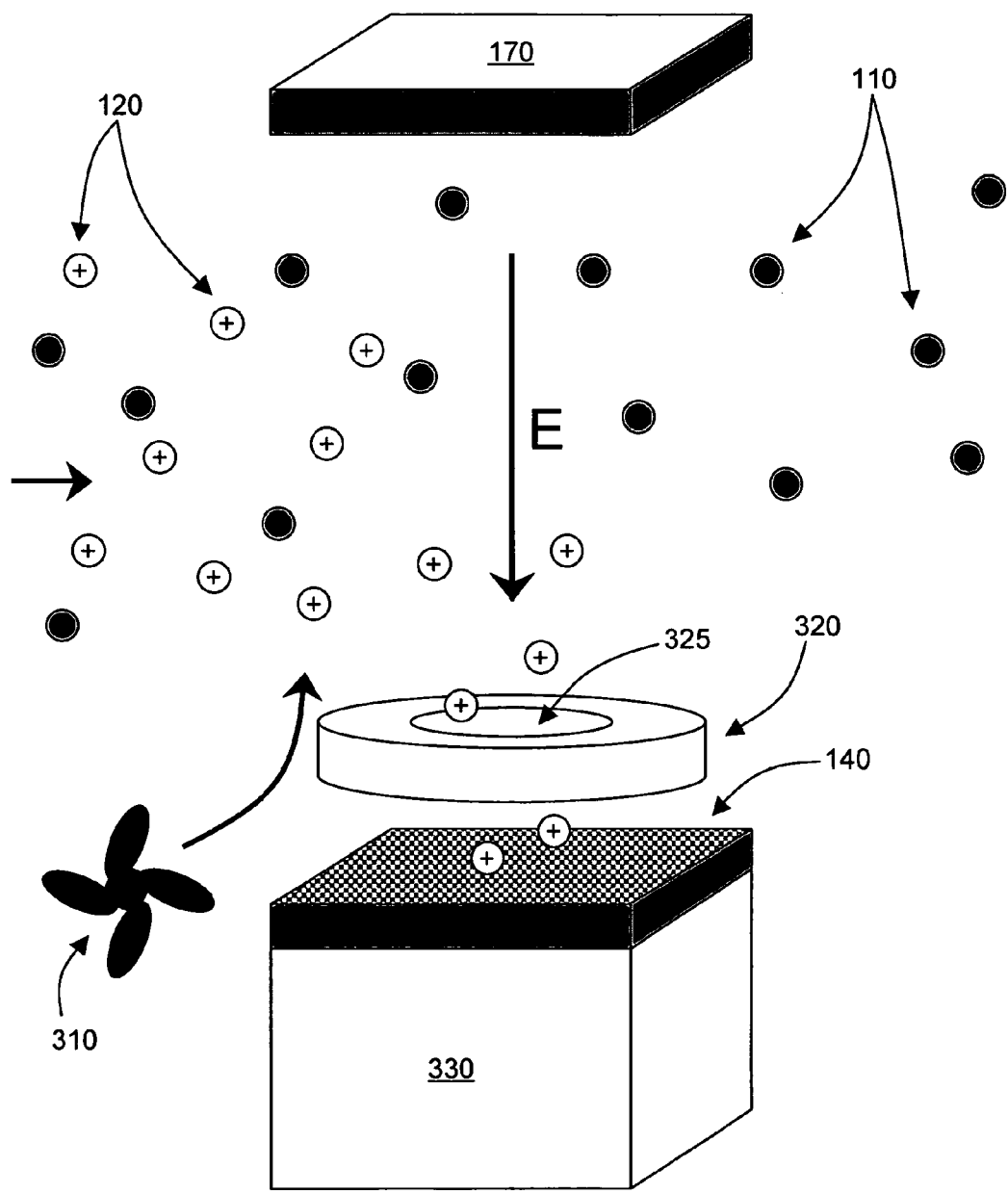
FIG. 3 shows cooling, focusing, and flow-producing components for the device of the present invention.

FIG. 3 shows an enlargement of the region near the SERS substrate 140 of an embodiment of the present invention with optional flow-producing 310, focusing 320, and cooling 330 components. The flowing gas of neutral particles 110 and ions 120 enters the region. A deflector electrode 170 and the SERS substrate 140 produce an electric field E to steer the ions to the SERS substrate 140. Neutral particles 110 are not affected by the electric field E and are ideally not deposited onto the SERS substrate 140. However, contamination of the SERS substrate 140 with neutral particles 110 can occur. A means for producing flow 310, such as a fan, away from the SERS substrate 140 reduces this contamination. When the electric field E is sufficiently strong, the ions 120 can be deposited onto the SERS substrate 140 despite the gas flow away from the substrate 140.

The sensitivity of the SERS system and the efficiency of the deposition of ions onto the SERS substrate 140 improve when the temperature of the SERS substrate 140 is lowered. FIG. 3 shows a cooling means 330 for cooling the SERS substrate 140. The cooling means 330 can be a container with liquid nitrogen in thermal contact with the SERS substrate 140, a Peltier refrigerator, a water cooling device, a fan, or any combination thereof.

FIG. 3 also shows an insulating wafer 320 for focusing the target ions onto a deposition area on the SERS substrate 140, where the deposition area can be less than the total area of the SERS substrate. By focusing the ions, the spectroscopic signal is enhanced from an increase in the density of target ions deposited. The insulating wafer 320 has a hole 325 where target ions can pass through and be directed toward the deposition area of the SERS substrate 140. The insulating wafer 320 deflects those ions with trajectories that do not pass through the hole 325. The hole 325 may be funnel-shaped or have multiple concentric rings to better direct the ions onto the deposition area of the SERS substrate 140 without deflecting a large number of stable target ions away. The insulating wafer 320 is preferably composed of Teflon.

Figure 4:
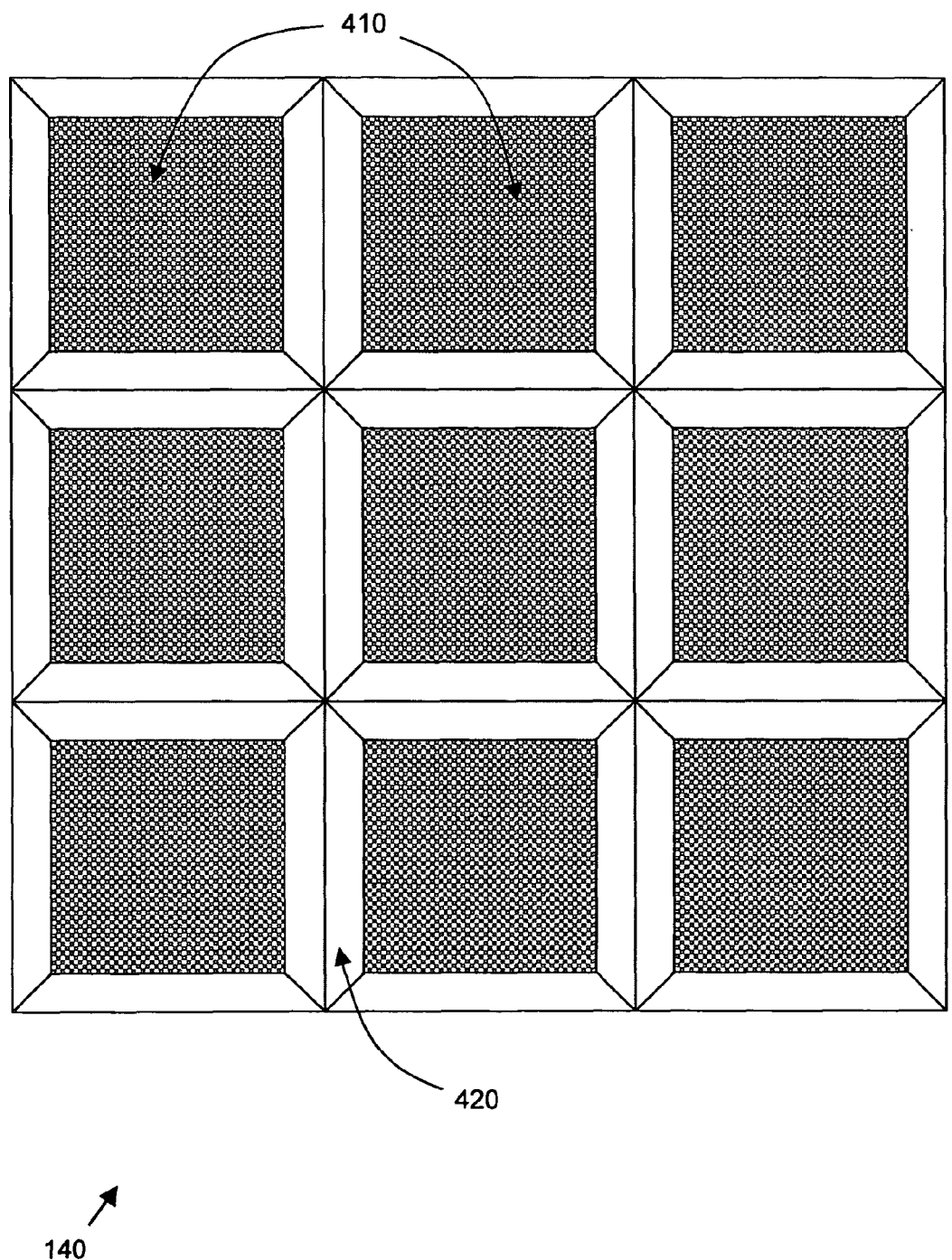
FIG. 4 shows an example of a SERS substrate with multiple segments according to the present invention.

Since the deposition area of the SERS substrate 140 is generally smaller than the size of the substrate, the SERS substrate 140 can be divided into multiple segments 410 to allow for multiple component analysis. FIG. 4 shows a SERS substrate 140 with segments 410 separated by insulators 420. Stable target ions can be deposited in each of the segments 410 and the optical probe 150 can measure a spectroscopic signal for each of the segments 410 separately. The number of distinct samples separated by the ion spectrometer could equal the number of segments 410 on the SERS substrate 140.

Optionally, each or a subset of segments 410 can be composed of a different material, such as different metals. The Raman response depends on the substrate material, therefore different materials could improve the identification of the sample. With or without varying the substrate material between segments 410, the optical probe settings, such as the laser light frequency and intensity, can be different for each segment 410. In addition, the division of multiple segments 410 allows for a more efficient use of the SERS substrate 140.

The device of the present invention is operable in a wide range of thermodynamic conditions. In particular, the device can be operated at a range of pressure from less than $10^{-6}$ Torr to $10^{15}$ Torr, preferably from about 600 Torr to about 1000 Torr. The temperature range can range from about 1 K to higher than about 600 K. Pressure and temperature gradients can also be present. In a preferred embodiment, the device operates at atmospheric pressure and room temperature.

As one of ordinary skill in the art will appreciate, various changes, substitutions, and alterations could be made or otherwise implemented without departing from the principles of the present invention, e.g. the computer of the SERS system can be substituted by any computing means, negative and positive ions can be detected, and one or more additional electrodes can be used as detector electrodes or for steering the target ions. Accordingly, the scope of the invention should be determined by the following claims and their legal equivalents.

What is claimed is:

1. A device for detecting and identifying ions from an ionized analyte, comprising:
   a) an ion separator for separating a plurality of target ions to be identified from a plurality of ion species ions, wherein said plurality of target ions and said plurality of ion species are formed in the ionization of said ionized analyte;
   b) a surface-enhanced Raman spectroscopy (SERS) system, comprising:
      i) a SERS substrate;
      ii) an optical probe; and
      iii) a computing means; and
   c) a means for establishing a voltage gradient, wherein said voltage gradient is for steering and depositing said target ions onto said SERS substrate,
   wherein said optical probe is for measuring a spectroscopic signal of said SERS substrate with said deposited target ions, and
   wherein said computing means is for identifying said target ions based on said spectroscopic signal.

2. The device as set forth in claim 1, further comprising a detector electrode for measuring an ion current of said target ions.

3. The device as set forth in claim 2, wherein said detector electrode comprises an electron multiplier, a photomultiplier, an amplification circuit, or any combination thereof.

4. The device as set forth in claim 1, wherein said SERS substrate comprises a detector electrode for measuring an ion current of said target ions, and wherein said measurement of said target ion current and said measurement of said spectroscopic signal can be accomplished approximately simultaneously.

5. The device as set forth in claim 1, wherein said ion separator comprises an ion filter for performing gas chromatography, liquid chromatography, or a combination thereof.

6. The device as set forth in claim 1, wherein said ion separator comprises a differential ion mobility spectrometer, an ion mobility spectrometer, a mass spectrometer, or any combination thereof.

7. The device as set forth in claim 1, wherein said ion separator comprises a differential ion mobility spectrometer (DMS), wherein said DMS is for separating said plurality of target ions from said plurality of ion species by applying a RF voltage and a DC compensation voltage, wherein said separation is based on said RF voltage and said compensation voltage, wherein said RF voltage produces an electric field ranging from about 0 V/cm to about 25000 V/cm, and wherein said compensation voltage produces an electric field ranging from about 20 V/cm to about 30 V/cm.

8. The device as set forth in claim 1, further comprising a means for applying a flow away from said SERS substrate, wherein said flow is for directing a plurality of neutral particles away from said SERS substrate.

9. The device as set forth in claim 1, further comprising an insulating wafer for focusing said target ions onto a deposition area of said SERS substrate, wherein said insulating wafer has a hole, and wherein said hole directs at least some of said target ions onto said deposition area of said SERS substrate.

10. The device as set forth in claim 1, further comprising a means for cooling said SERS substrate, wherein said cooling means is a container with liquid nitrogen in thermal contact with said SERS substrate, a Peltier refrigerator, a water cooling device, a fan, or any combination thereof.

11. The device as set forth in claim 1, wherein said SERS substrate comprises a plurality of segments, wherein said segments are separated by one or more insulators, wherein said target ions can be deposited on each of said plurality of segments, and wherein said optical probe can measure a spectroscopic signal of each of said plurality of segments separately.

12. The device as set forth in claim 1, wherein said ionized analyte comprises an explosive, a home-made explosive, a flammable liquid, a chemical warfare agent, a chemical agent, a biological agent, a biochemical agent, a toxic industrial chemical, a toxic industrial material, an organic material, a trace element, or any combination thereof.

13. A method for detecting and identifying ions from an ionized analyte, comprising:
  a) separating a plurality of target ions to be identified from a plurality of ion species, wherein said plurality of target ions and said plurality of ion species are formed in the ionization of said ionized analyte, and wherein said separating is accomplished with an ion separator;
  b) steering and depositing said target ions onto a surface-enhanced Raman spectroscopy (SERS) substrate;
  c) measuring a spectroscopic signal of said SERS substrate, wherein said target ions are deposited onto said SERS substrate; and
  d) identifying said target ions based on said spectroscopic signal.

14. The method as set forth in claim 13, further comprising measuring the current of said target ions.

15. The method as set forth in claim 14, wherein said measurement of said target ion current and said measurement of said spectroscopic signal are accomplished approximately simultaneously.

16. The method as set forth in claim 13, wherein said ion spectrometer comprises a differential ion mobility spectrometer, an ion mobility spectrometer, a mass spectrometer, or any combination thereof.

17. The method as set forth in claim 13, wherein said ion separator comprises a differential ion mobility spectrometer (DMS), wherein said DMS is for separating said plurality of target ions from said plurality of ion species by applying a RF voltage and a DC compensation voltage, wherein said separation is based on said RF voltage and said compensation voltage, wherein said RF voltage produces an electric field ranging from about 0 V/cm to about 25000 V/cm, and wherein said compensation voltage produces an electric field ranging from about 20 V/cm to about 30 V/cm.

18. The device as set forth in claim 13, further comprising focusing said target ions onto a deposition area of said SERS substrate.

19. The method as set forth in claim 13, further comprising applying a flow away from said SERS substrate, wherein said flow is for directing a plurality of neutral particles away from said SERS substrate.

20. The method as set forth in claim 13, further comprising cooling said SERS substrate.

* * * * *